United States Patent [19]

Shaffer

[11] 4,142,859

[45] Mar. 6, 1979

[54] CHEMILUMINESCENT PROCESS AND DETECTOR FOR MONITORING ATMOSPHERIC CONTAMINANTS

[75] Inventor: Roy E. Shaffer, Bel Air, Md.

[73] Assignee: The United States of America as represented by the Secretary of the Army, Washington, D.C.

[21] Appl. No.: 809,353

[22] Filed: Jun. 23, 1977

[51] Int. Cl.[2] .......................... G01J 3/46; G01N 21/26

[52] U.S. Cl. ............................ 23/232 R; 195/103.5 L; 195/127; 356/410; 422/86; 422/88

[58] Field of Search ............. 23/232 R, 230 B, 254 R; 195/103.5 L, 127; 356/180, 181, 201

[56] References Cited

U.S. PATENT DOCUMENTS

| | | | |
|---|---|---|---|
| 3,659,100 | 4/1972 | Anderson et al. | 23/232 R |
| 3,690,832 | 9/1972 | Plakas | 23/230 B |
| 3,748,044 | 7/1973 | Liston | 356/180 |
| 3,833,304 | 9/1974 | Liston | 356/188 X |
| 3,940,250 | 2/1976 | Plakas | 23/230 B |

*Primary Examiner*—Morris O. Wolk
*Assistant Examiner*—Arnold Turk
*Attorney, Agent, or Firm*—Nathan Edelberg; Robert W. Church

[57] ABSTRACT

Process and device for detecting impurities in the atmosphere by an intensity-time rate technique whereby chemiluminescent reaction curves are developed and found to be representative of specific materials. Hence, by comparing known intensity-time rate curves with curves had by actual measurings, the invention enables the user to discern many more materials never before detected.

11 Claims, 8 Drawing Figures

CHEMILUMINESCENT PROCESS AND DETECTOR FOR MONITORING ATMOSPHERIC CONTAMINANTS

DEDICATORY CLAUSE

The invention described herein may be manufactured, used or licensed by or for the United States Government without the payment to me of any royalty therefor.

BACKGROUND OF THE INVENTION

My invention deals with a new process and device for the measuring of impurities such as biologicals in the breathing atmosphere.

The one known prior art process and device for the measurement of biologicals has proven inaccurate and has been discarded for that reason. It comprised a process of measuring the reactive material in the measured medium by measuring light intensity thereof. This is done by mixing chemiluminescent chemicals and oxidizers with the medium to be measured. Then a photo tube is used to measure the light intensity. In other words, the presence of microbiological organisms or other matter is detectable but discernment stops there. A need has existed for the detection of specific materials, however, until my invention, this end has not been met.

It has been known since 1928 (Albricht) about the chemiluminescence of luminol (5 amino 2-3 dehydro - 1-4 phthalazinedione). The slow luminescence induced by hydrogen peroxide can be increased by a catalytic agent such as heme. Heme is the iron containing porphyrin molecule found in both animal and plant cells. It is also the pigmented oxygen carrying part of hemoglobin. Hence, if some common ingredient like heme is present in all proteinaceous material, it provides an excellent base for the detection of bacteria and viruses. This is done by the use of chemiluminsecent reaction. It should be noted that although heme is not theoretically present in pure virus, it is present in virus-containing substrate which generally consist of animal tissue. Henfeld et al article from Analytical Biochemistry, Vol. 12, No. 2, of August 1965 by Academic Press, Inc. has demonstrated that the intensity of the luminescence is a fuction of the concentration of the heme catalyst. He has suggested and used this method in the detection of heme-containing materials.

One aspect of my invention is that I have found that for different materials the intensity versus time for chemiluminescent reaction curves is different. This has opened up the new era of separating materials into groups, i.e., all those materials displaying substantially the same reaction curve are grouped together. Hence, I have been able to discern undetectable substances heretofore never singled out or noted with the use of chemiluminescence.

Briefly, my invention involves a new device and process for measuring the presences of biologicals and similar impurities in the atmosphere. I use the chemiluminescence reaction and measure luminescence versus time. I use an alkaline solution of luminol, an oxidant and a catalyst. I cause the luminol and sodium perborate to be mixed together, pick up a sample containing heme as aforesaid and carry the sample by way of a water carrier to the aforementioned mixed ingredients. Then I mix all components thereof and monitor the light intensity and the duration of such intensity and plot a curve thereof. Once I've sampled and plotted numerous known materials by way of lumination versus time then to detect an unknown, I need only compare the plot to prior curves.

It is therefor an object of my invention to detect materials in the atmosphere by the use of a chemiluminescent reaction and an intensity versus time measurement thereof.

A further object of my invention is to detect materials in the atmosphere with a process and apparatus using a chemiluminescent reaction and an intensity versus time measurement thereof.

Another object of my invention is to detect proteinaceous material in the atmosphere with a process and appparatus using chemiluminescent reaction and an intensity versus time measurement thereof.

Other objects and advantages of my invention will occur to one skilled in the art as he peruses the following description and drawings.

THE DRAWINGS

FIG. 1 view of my detection apparatus showing various interconnections therewith.

SPECIFIC EMBODIMENT

Figure 1:
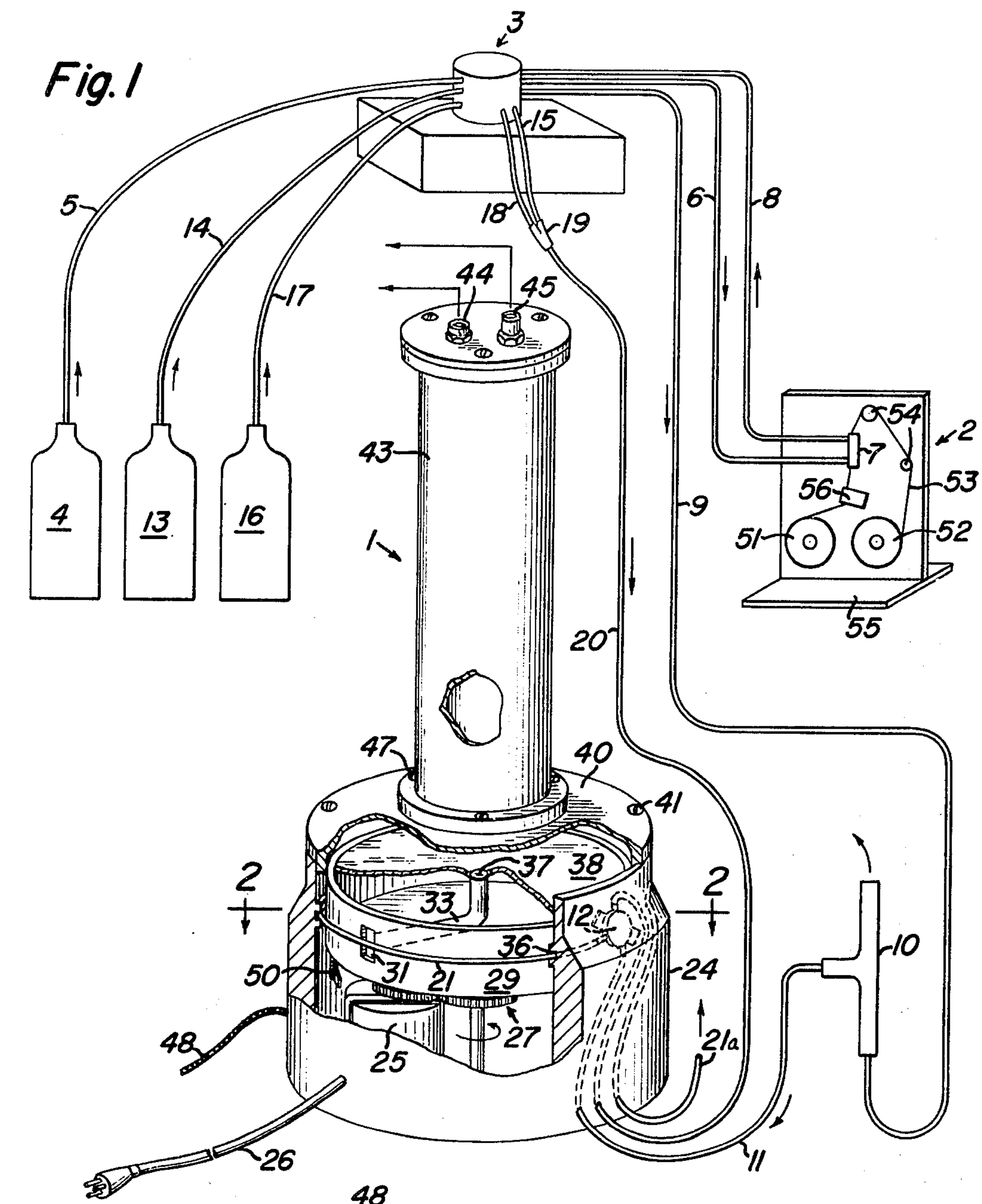

To best describe my invention, the preferred embodiment of my invention is as follows: FIG. 1 shows the major portion of my biological detection system with conventional equipment such as a scope or recorder not shown. The choice of a scope or recorder of course will depend upon output signal speed from my invention photo tube to be described below.

Referring to FIG. 1, numeral 1 is my time rate device. Numeral 2 is our sample gathering assemblage or bread board unit shown in block like form. Numeral 3 is a polystatic pump assemblage shown in a general form which functions to move the various fluids as shown. Pump 3 is a gang unit which moves plural fluids at like speeds through isolated passages. From water supply 4 by way of tube 5 water is moved by way of pump 3 to and thru tube 6 to wash head 7 where it is caused to pick up a sample and carry same in tube 8 back through the pump to and through tube 9 to bubble trap 10 where the bubbles are removed. From trap 10 the sample is carried by the water through tube 11 to mixing chamber 12 where the other ingredients to be described are mixed therewith. Luminol supply 13 is pumped by way of tube 14 through pump 3 to tube 15. Sodium perborate is pumped from supply 16 through tube 17 by pump 3 to tube 18. Pump 3 forces the luminol in tube 15 and the sodium perborate in tube 18 to mixer tee 19 whereat they are mixed and forced by pump 3 through tube 20 to mixer 12 of time rate device 1. From mixer chamber 12 after the water, luminol, sodium perborate and sample are mixed, the resultant mixture is forced through transparent tube 21 of the time rate device. After traversing the circumference of the device 1 by way of tube 21 the mixture passes to waste tube portion **21*a*** and the material is discarded thereafter.

Figure 7:
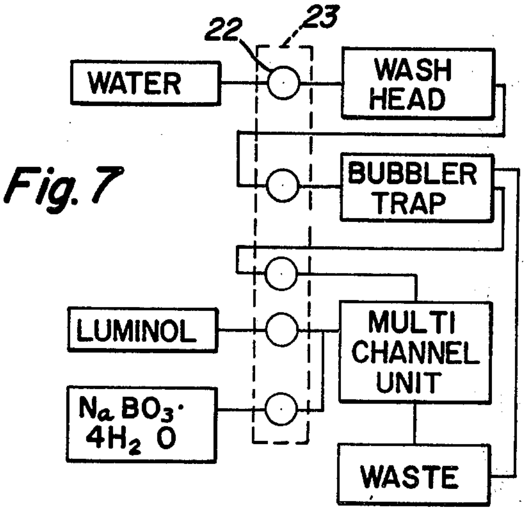
FIG. 7 is a block diagram of my fluid flow in my invention.

Referring to FIG. 7 it is noted herein is shown a flow chart of how the various fluids flow. Note circles 22 in dashed block 23 represent pump 3 of FIGS. 1 and 3 and the various lines are tube interconnections. The ingredients are spelled out and shown in representative blocks.

Figure 3:
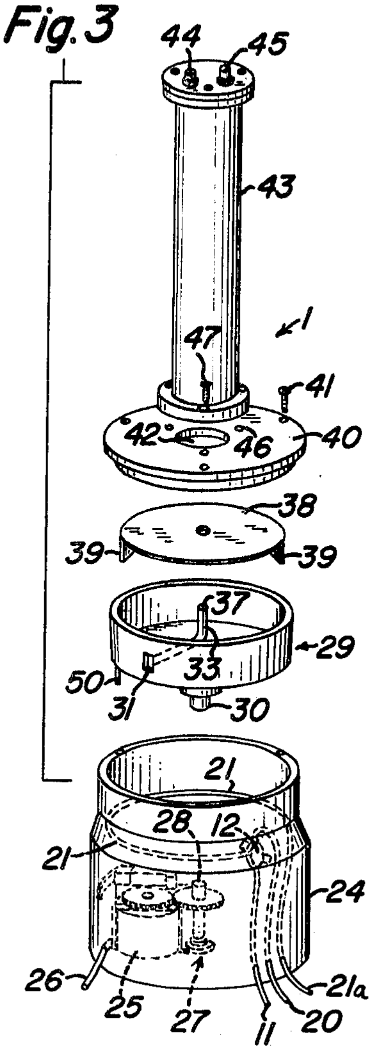
FIG. 3 is an exploded view of my detection device.
Figure 4:
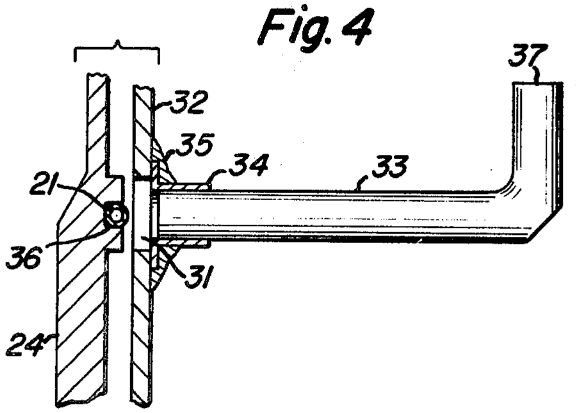
FIG. 4 is a section view showing the optic assemblage of my device.

FIG. 3 is an exploded view of my time rate device 1. Housing 24 of metal houses motor 25 which furnished appropriate electricl power by way of cord 26. Housing 24 can be provided with appropriate orifices (not shown) for motor cooling, etc., if desired. Gearing assemblage 27 has drive adaptor 28 thereon for engaging and turnably driving and supporting rotating dish 29 at 30. Dish 29 is preferably of metal though it can as well be of opaque plastic material. It is provided with optical hole 31 which enables light to travel through wall 32 of dish 29 (see FIG. 4). Fiber optic rod 33 is fixedly mounted to wall 32 by way of adaptor 34 with appropriate adhesive 35. Dish 29 rotates and in this instance is 6 inches in diameter and must rotate within housing 24. Tube 21 of transparent plastic material is affixed to the inside of housing 24 at slot 36 by appropriate adhesive (see FIG. 4 for an exploded view thereof). Fiber optic rod 33 extends to the center of dish 29 and is upraised at 37. Overlaying rod 33 with portion 37 extending therethrough, i.e., when assembled (see FIG. 1) is light cover 38 with stirrup 39. Stirrups 39 hold cover 38 upright and properly oriented in element 29. Removably enclosing rotating dish 29 and light cover 38 is housing cover 40 which is secured to housing 24 by cap screws 41. Note housing cover 40 has aperture 42 through which light can pass from portion 37 of fiber optic rod 33 to the photo tube 43. Photo tube 43 is a EMI 9635B made by the Electrical Mechanical Instruments Company. Photo tube 43 has terminals 44 and 45 through which the output signal in milivolts passes and the input tube voltage is applied, respectively. Photo tube 43 is secured to housing cover 40 at 46 by screws 47.

Figure 5:
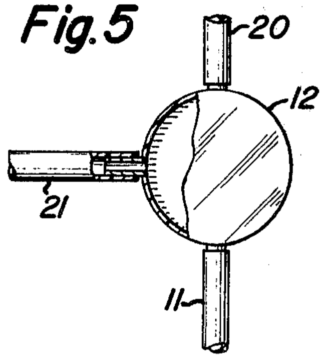
FIG. 5 is the mixing chamber of my detector.

FIG. 5 depicts mixing chamber 12 enlarged with tubes 21, 11 and 20 affixed.

Figure 2:
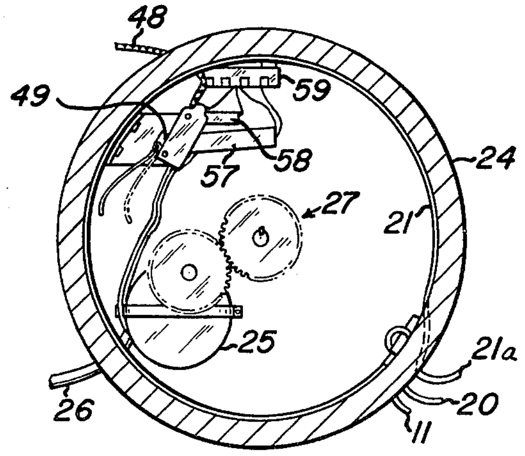
FIG. 2 is a cross section of the lower section of my detection device.

FIG. 2 is a bottom view of the time and rate device 1. Motor 25 and the gear assemblages 27 are shown thereat along with a limit switch 49 which triggers the scope or recorder at each revolution of dish 29 at 50. That is, the switch 49 arm engages leg 50 of dish 29. The gearing assemblage reduces the speed of rotation so that dish 29 rotates at the same velocity that the fluid mixture from mixing chamber 12 flows through tube 21 around the inside of housing 24.

Bread board unit 2 depicted on the right most portion of FIG. 1 for the same of illustration is shown in a simplified manner. It comprises sample pick up tape 53 being passed by motor means not shown from virgin tape reel 51 through and past sample pick up means 56 which has high pressure sample containing air being blown thereat on tape 53, then tape 53 is drawn past wash head 7 over idlers 54 to pick up reel 52. Idlers 54 and reels 51 and 52 as well as tape 53 are movable on support 55. When tape reel 52 is exhausted a new tape 53 and associated reel 51 are substituted therefor.

In FIG. 2 as well as FIG. 1 element 48 is a thermocouple that extends inside housing 24 adjacent to tube 21 to measure the mixture temperature. It can be secured in any manner. The output of the thermocouple is sent to the recorder by way of milivolt output. This monitors the temperature. Element 58 is a capacitor of 0.01m fd. and element 57 is a 100 ohm resistor tied into an RC circuit at terminal block 59. A wire not shown should be connected from terminal 44 on tube 43 to this RC circuit and then therefrom the output should be sent to the recorder.

OPERATION

The operation of my system shall now be explained. I provide water in supply 4 an alkaline solution (pH 13) of luminol in supply 13 and an oxidant sodium perborate in supply 16 and a sample micro organism is found on tape 53 after it passes means 56. Pump 3 forces water into washing head 7 by way of tube 6 and out tube 8 picking up the sample and carrying it into tube 8. From tube 8 sample carrying water is sent through tube 8 to the bubbler 10 where the bubbles are removed at the upper orifice thereof. Tube 11 then carries the water laden sample to mixing chamber 12. Contemporaneous therewith pump 3 draws 0.04 molar of luminal solution through tube 14 to tube 15 and 0.1 molar of sodium perborate solution from supply 16 to 18 whereat the components are forced through mixing Tee 19. Here they are mixed and the mixed solution sent through tube 20 on to mixing chamber 12.

Figure 6:
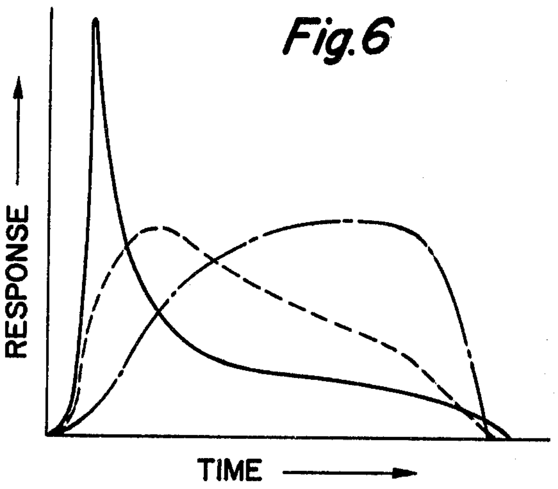
FIG. 6 depicts various plots or curves for detecting.

At chamber 12 a final mixture of luminol, sodium perborate, water and the heme sample are mixed. From chamber 12 the final mixture is flowed through tube 21 at a rate commensurate with the dish 29 velocity. Simultaneously, motor 25 is caused to rotate dish 29 by way of adaptors 28 and 30 at 6 RPM. The light resulting from the luminal reaction is picked up by the fiber optic 33 and transferred to the photo tube 43. Thus any variation of the lumination by the reaction heme will be continuously monitored for one revolution of the dish 29. This is done by way of opening 31 fiber optic 33 and portion 37 and photo tube 43. Any variation will be forwarded to terminal 44 by way of an electrical signal. The signal will then be sent through RC circuit 57, 58 on to the recorder. It will then appear as the line dot curve shown in figure 6. The limit switch 49 when its arm is hit by rotation of element 50 of dish 29 can then be used to signal a recorder or scope. It should be noted that a conventional power supply can be used to supply high voltage to the photo tube 43 terminal 45. The photo tube 43 of course measures light intensity and transforms it as electrical energy. In the above example, if a metal ion sample is picked up by tape 53 the solid line curve of FIG. 6 would result. If a more reactive heme containing protein tissue sampe were picked up on tape 53 the dashed curve of FIG. 6 would result.

It should be noted since the time rate device 1 depends on light sensitivity, all components must be so compatible, i.e., the light cover 38 cannot pass light.

Any conventional oscilloscope, recorder can be used in my system. Element 2 the bread board tape unit can take various shapes. The head element is a tube with a tape slit for the tape to pass therethrough. Tubes are joined at the ends. The tape is Mylar with particle adhering tacky adhesive thereon. The reels are turned so as to move the tape an inch a minute. Appropriate motor gearing, etc., is within one skilled in the arts realm.

In the case of luminol and sodium perborate, any reference thereto should incorporate the fact that they are in water and form a solution.

Figure 8:
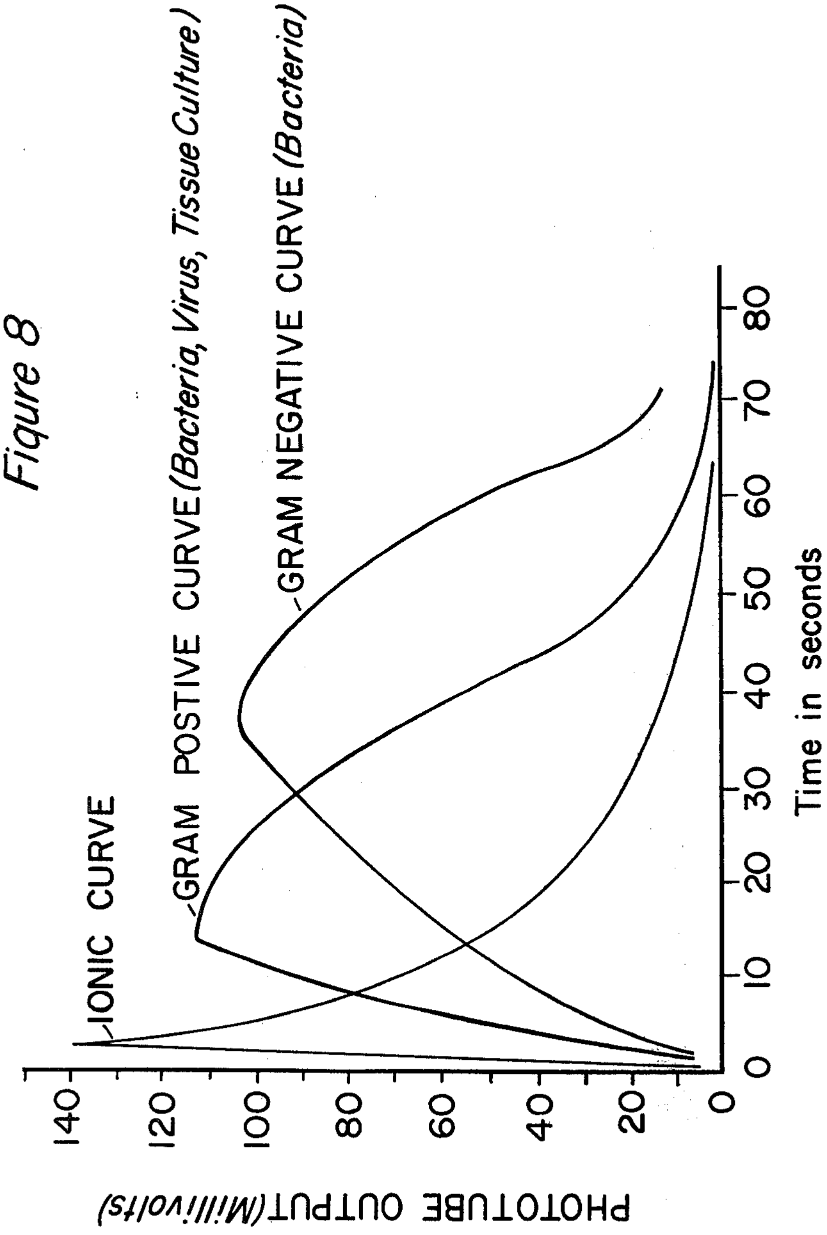
FIG. 8 is a Table indicating the time rate chemiluminescence response to various materials.

The time rate curves in FIG. 8 are typical of the experimental results. The reaction can be catalyzed by metallic ions as well as heme-containing biological materials. Metallic ions produce a very rapid flash, while the flash rate for gram-positive bacteria represents a slower reaction. The reaction of gram-negative bacteria is slower than that for gram-positive organisms. The shape of a particular chemiluminescent response curve can be represented by a scoring system. Each curve consists of 30 equally spaced points numbered 1 to 30. The area under each curve is normalized by dividing each point by the sum of all 30 points. Each normalized point is then divided by its ordinal number and summed to obtain a score. The score is multiplied by 1000 to provide a range of 33.33 to 1000.

The score range is shown in Table 1. Scores of 0 to 125 represent gram-negative bacteria. Scores of 125 to 225 represent gram-positive bacteria, tissue culture materials and virus. The range of metal ions is above 225. The scores can therefore distinguish between three groups of substances. The differentiation between members within the group is more difficult. The score (from Table 1) for for *marcescens* is 80 and for *Salmonella typhimurium* 95. These organisms can be distinguished from each other, but only under rigidly controlled conditions. The *Klebsiella pneumonia,* having a score of 100, cannot be separated from *Escherichia coli,* score of 101. These could, however, be distinguished with ease from gram-positive Bacilli, virus or tissue cultures.

The scoring system presently in use is biased towards the front of the curve. Other logic systems including one that gives equal emphasis to the front and back portions of the curve may improve identification resolution of bacteria and other biological materials. Separation of metal ions from biological material is specific and definite. Resolution based on score can thus be obtained in the metal ion group. The virus scores generally reflect their substrate material. Tissue culture can be separated from gram-positive bacteria. The spore form of a gram-positive bacteria gives a gram-negative score while the vegetative form gives a gram-positive score. The concentration of bacteria necessary for a reliable score determination appears to be from $10^5$ to $10^6$ cells per milliliter.

The viability of the cells does not affect the catalytic ability of the heme.

The difference in response between the bacterial spore and the vegetative form suggests that the permeability of the cell wall may determine the characteristic reaction. If this latter is true then all curves would be similar if permeability differences were eliminated. If the response is due to differences in the type of heme catalyst, the curves will not be similar or identical but will retain their characteristic form. Table 2 shows the results for substances treated with 0.1N NaOH for five minutes. It can be seen that all the scores approach unanimity (scores for the upper limits of the gram-positive group). Metal ion curve scores did not change when treated. The intensity of the response to all substances increased with sodium hydroxide treatment and in most cases the response amplitude was doubled. This indicates that more heme became available during treatment. The time for reaching peak voltage was the same for all biological material. Sodium hydroxide treatment for a longer time period did not change the score of peak time. The longer time period did, however, reduce the peak voltage response. This could be due to denaturization of the heme material. The metal ions were not affected by the longer treatment either in score, time of peak response, or intensity of peak response.

These observations would tend to indicate that it is cell wall permeability that determines the curve form and not differences in heme structure. Many substances affect the permeability of the cell wall or the availability of the heme. Distilled water affects permeability more than physiological saline, but less than 0.1N NaOH. All dilutions and suspensions were made in distilled water as a standard practice.

The temperature of the reaction affects the reaction rate curve of biological substances and metal ions. Table 3 presents results of three different reaction temperatures on biological materials and metal ions. The biological curves have not yielded identical forms as in the case of the sodium hydroxide treatment. The change in temperature does not have an affect on peak voltage of biological materials. An increase from 3° C. to 45° C. produces a 5 to 10 fold increase in peak voltage. The scores increase but do not approach unanimity. The time to peak voltages of biological material becomes shorter with increases of temperature. The time to peak voltage with metal ions does not change with increased temperature. The changes observed with increases in temperature are primarily changes in reaction rate. There is some indication that increases in temperature affect cell wall permeability. This is observed at 45° C. where a much shorter time is required to reach peak voltage.

The standard reactions are conducted at 15° C. The scores reflect maximum separation of biological groups and metal ions at this temperature. The peak voltages developed at these temperatures are sufficient to produce good curve definition at cell concentrations of $10^5$ to $10^6$ bacteria per milliliter.

The chemiluminescence reaction can differentiate broad groupings of biological substances from metal ions. Biological materials can be further separated into two main groups: (1) gram-negative bacteria and (2) gram-positive bacteria and viruses. Gram-positive bacteria and viruses can be separated into subgroups with some exceptions. A scoring system has been developed to describe the time rate curves and thus facilitate differentiation of biological substances as well as metallic ions. The reaction appears to depend on the availability of heme and not upon structural or other differences. The temperature of the reaction affects the results with respect to response intensity and differentiation of broad groups of substances.

Standard test conditions include the use of distilled water as a suspending medium and a reaction temperature of 13° C. to 19° C.

TABLE 1

TIME RATE CHEMILUMINESCENCE SCORES FOR VARIOUS MATERIALS*

| MATERIAL | CLASS | SCORE | PEAK TIMES | SCORE RANGE |
|---|---|---|---|---|
| 1) *SERRATIA MARCESCENS* | BACTERIA GRAM NEGATIVE | 80 | 36 sec | 0 |
| 2) *SALMONELLA TYPHIMUNIUM* | BACTERIA GRAM NEGATIVE | 95 | 30 sec | |
| 3) *KLEBSIELLA PNEUMONIAE* | BACTERIA GRAM NEGATIVE | 100 | 32 sec | |
| 4) *ESCHERICHIA COLI* | BACTERIA GRAM NEGATIVE | 101 | 28 sec | |

TABLE 1-continued

| | TIME RATE CHEMILUMINESCENCE SCORES FOR VARIOUS MATERIALS* | | | |
|---|---|---|---|---|
| MATERIAL | CLASS | SCORE | PEAK TIMES | SCORE RANGE |
| 5) *FRANCISELLA TULARENSIS* | BACTERIA GRAM NEGATIVE | 122 | 13 sec | 125 |
| 6) *STREPTOCOCCUS PNEUMONIAE* | BACTERIA GRAM POSITIVE | 127 | 22 sec | |
| 7) *BACILLUS SUBTILIS* | BACTERIA GRAM POSITIVE | 144 | 11.4 sec | |
| 8) VEE (TC 83) | VIRUS | 142 | 11 sec | |
| 9) INVLUNEZIA A-2 | VIRUS | 151 | 10.6 sec | |
| 10) CHICK FIBER BLAST | TISSUE CULTURE | 167 | 6.8 sec | |
| 11) BABY HAMSTER | TISSUE CULTURE | 204 | 4.8 sec | 225 |
| 12) $FeCl_3$ | ION | 362 | 2.3 | |
| 13) $CuSO_4$ | ION | 564 | 4.5 sec | |
| 14) $V_2O_5$ | ION | 676 | 4.5 sec | |

*REACTION CONDUCTED AT 14° C.

TABLE 2

| | TIME RATE CHEMILUMINESCENT RESPONSE OF MATERIALS WITH 0.1 N NaOH* | | | | | |
|---|---|---|---|---|---|---|
| | 0 | NaOH | | | 0.1 NaOH for 5 min | |
| MATERIAL | PEAK VOLTAGE IN MILLIVOLTS | PEAK TIME IN SECONDS | SCORE | PEAK VOLTAGE IN MILLIVOLTS | PEAK TIME IN SECONDS | SCORE |
| 1) HEMOGLOBIN | $2.6 \times 10^6$ | 10 | 161 | $98 \times 10^6$ | 7 | 198 |
| 2) *BACILLUS MEGATHERIUM* | $26 \times 10^3$ | 10 | 147 | $92 \times 10^3$ | 5 | 218 |
| 3) *ESCHERICHIA COLI* | $9.1 \times 10^5$ | 23 | 103 | $1.5 \times 10^6$ | 7 | 198 |
| 4) *SERRATIA MARCESCENS* | $6 \times 10^4$ | 23 | 81 | $1.3 \times 10^6$ | 7 | 225 |
| 5) *STAPHYLOCOCCUS EPIDERMIDIS* | $3 \times 10^4$ | 10 | 127 | $2.4 \times 10^5$ | 7 | 219 |
| 6) BABY HAMSTER KIDNEY TISSUE CULTURE | $7 \times 10^4$ | 7 | 177 | $2.3 \times 10^5$ | 7 | 217 |
| 7) $FeCl_3$ | $8.3 \times 10^4$ | 2.3 | 312 | $7.0 \times 10^4$ | 2.3 | 310 |

*REACTION CONDUCTED AT 17° C

TABLE 3

| | TIME RATE CHEMILUMINESCENT RESPONSE OF MATERIAL AT DIFFERENT TEMPERATURES TEMPERATURE OF REACTIONS | | | | | | | | |
|---|---|---|---|---|---|---|---|---|---|
| MATERIAL | SCORE | 3° C TIME IN SECONDS | PEAK VOLTAGE MILLI-VOLTS | SCORE | 25° TIME | PEAK VOLTAGE MILLI-VOLTS | SCORE | 45° C TIME IN SECONDS | PEAK VOLTAGE MILLI-VOLTS |
| 1) HEMO-GLOBIN | 87 | 23 | 59 | 181 | 9 | 438 | 402 | 7 | 1083 |
| 2) *BACILLUS MEGATH-ERIUM* | 119 | 23 | 85 | 190 | 9 | 531 | 185 | 7 | 836 |
| 3) *ESCHERIA COLI* | 80 | 37 | 659 | 127 | 10 | 2077 | 212 | 9 | 3291 |
| 4) *SERRATIA MARCES-CENS* | 65 | 70 | 199 | 176 | 14 | 1730 | 283 | 9 | 3901 |
| 5) *STAPHYLO-COCCUS EPIDER-MIDIS* | 87 | 25 | 196 | 137 | 14 | 904 | 187 | 9 | 2412 |
| 6) FETAL BOVIN SERUM | 98 | 25 | 127 | 181 | 7 | 376 | 158 | 7 | 783 |
| 7) $FeCl_3$ | 147 | 2.3 | 87 | 262 | 2.3 | 829 | 191 | 2.3 | 126.7 |

In summary in the use of my device 1, the rate the fluid flows in tube 21 should be equal to the rate the dish 29 rotates so that the fiber optic monitors the same fluid portion on one revolution.

Accordingly, it should be understood that the particular embodiment of the invention shown in the drawings described above are intended to be illustrative only and not intended to limit the scope of the invention.

I claim:

1. A system for monitoring of materials in a time-intensity rate fashion comprising:

an annular sample carrier system adapted to be monitored;

a sample disposed in said system;

monitoring means centerly located and rotatable within and in the direction of said carrier for time rate optically monitoring said sample; and means for moving said sample in said system at a rate commensurate with that of said monitoring means for time-intensity rate measurement.

2. The invention of claim 1 wherein sample includes reaction chemicals.

3. The invention of claim 2 wherein said optical monitoring means includes fiber optic means for transmitting light to a photo-tube.

4. The invention of claim 3 wherein said optics are oriented to pick up light resulting from reactions in said annular carrier system.

5. The invention of claim 4 wherein said annular carrier system comprises at least one transparent tube.

6. The invention of claim 5 wherein said sample including reaction chemicals is in a fluid state and said means for moving is a pump.

7. The invention of claim 6 wherein said sample is disposed within the system by tape means.

8. A process of monitoring contaminants in the atmosphere comprising the steps of:

disposing a sample of the atmosphere in a water carrier and mixing it with luminous type reactants, measuring and graphing the luminous reactions for a time frame; and comparing the graph shape with known samples to ascertain the makeup of said sample.

9. The invention of claim 8 wherein said disposing step is by tape means and said mixing step includes material such as sodium perborate, luminol and water.

10. The invention of claim 8 wherein said measuring for a time frame is achieved by rotating a monitoring means at a rate commensurate with the rate of flow about an annular tube arranged therearound.

11. The invention of claim 10 wherein said mesuring is further made with light optics and a photo tube to facilitate the graphing which is done by an electronic recorder.

* * * * *